(12) United States Patent
Miroshnychenko et al.

(10) Patent No.: US 7,496,177 B2
(45) Date of Patent: Feb. 24, 2009

(54) X-RAY CONVERTER

(76) Inventors: Sergii Ivanovych Miroshnychenko, 58 Dmitrovskaya St., apt. 4, Kiev, 01054 (UA); Yevgen Olegovych Zhilko, 30/51 Ozernaya St., apt. 156, Kiev, 04209 (UA); Volodymyr Volodymyrovych Kulakov, 94 Pravdy Ave., apt. 110, Kiev, 04208 (UA); Andrii Olexandrovych Nevgasymyi, 18 Generale Zchmachenko St., apt. 364, Kiev, 02192 (UA); Olexandr Olexandrovych Redchuk, 19 Chernyahovskogo, apt. 82, Brovary, 07400 (UA)

( * ) Notice: Subject to any disclaimer, the term of this patent is extended or adjusted under 35 U.S.C. 154(b) by 126 days.

(21) Appl. No.: 11/662,149

(22) PCT Filed: Jan. 5, 2005

(86) PCT No.: PCT/AU2005/000002

§ 371 (c)(1),
(2), (4) Date: Mar. 6, 2007

(87) PCT Pub. No.: WO2006/049589

PCT Pub. Date: May 11, 2006

(65) Prior Publication Data

US 2007/0297568 A1 Dec. 27, 2007

(30) Foreign Application Priority Data

Nov. 5, 2004 (UA) .............................. 20041109064

(51) Int. Cl.
*H05G 1/64* (2006.01)
*G21K 3/00* (2006.01)

(52) U.S. Cl. ...................... 378/98.3; 378/98.8; 378/156
(58) Field of Classification Search ................ 378/98.3, 378/98.9, 156, 157, 189–191; 250/370.09
See application file for complete search history.

(56) References Cited

U.S. PATENT DOCUMENTS 4,208,577 A 6/1980 Wang (Continued)

OTHER PUBLICATIONS

International Search Report dated Aug. 3, 2005 PCT AU/2005/000002.

*Primary Examiner*—Irakli Kiknadze
(74) *Attorney, Agent, or Firm*—Abelman, Frayne & Schwab

(57) ABSTRACT

An X-RAY CONVERTER having a light-proof housing with an X-ray-transparent wall behind which there are fastened an X-ray-to-optical converter, a filter of residual X-radiation, an objective lenses unit, and a photodetector containing at least two optoelectronic converters with partly overlapping fields of view and separated electrical outputs for connection to a system for processing of fragmentary video signals and generating an integral output video signal. For improving the efficiency of suppression of internal interferences in optical channels and the operating reliability, within the housing, parallel to the X-ray-to-optical converter, there is rigidly fastened an additional light- and X-ray-opaque partition with through-holes which in the number and placement correspond to objective lenses and optoelectronic converters and are blocked by washers of the filter of residual X-radiation, and ahead of the washers there are installed blinds, length A of each of which and distance D from the front surface of the X-ray-to-optical converter to the plane of front end faces of objective lenses are related by the ratio A/D=(0.50 . . . 0.95).

16 Claims, 2 Drawing Sheets

U.S. PATENT DOCUMENTS

| | | |
|---|---|---|
| 5,719,623 A | 2/1998 | Kinoshita et al. |
| 6,002,743 A | 12/1999 | Telymonde et al. |
| 6,370,225 B1 | 4/2002 | Telymonde |
| 6,507,638 B2 * | 1/2003 | Curtis et al. ............... 378/98.3 |
| 6,936,823 B2 * | 8/2005 | Sauvage et al. ............. 250/368 |
| 7,035,372 B2 * | 4/2006 | Chen ........................... 378/62 |
| 7,053,382 B2 * | 5/2006 | Noji et al. ............... 250/370.11 |
| 7,135,686 B1 * | 11/2006 | Grady ................... 250/370.11 |

* cited by examiner

X-RAY CONVERTER

FIELD OF THE INVENTION

The invention relates to structure of an X-ray converter based on at least two such optoelectronic converters as television camera (hereinafter, TV camera), photodiode matrix, etc. These converters are used in X-ray apparatus:

for diagnostic angiographic examinations using X-ray contrast substances, in particular, for determining of vessels' passability and efficiency of blood supply of organs and tissues, for locating of probes, catheters, and other diagnostic or surgical instruments introduced into the body through blood vessels, trachea and bronchial tubes, esophagus, anus, and other tubular organs, for a repeated roentgenography of lungs, heart, stomach, and other (in particular, movable) organs, for a filmless roentgenography in traumatology, for a filmless photofluorography at mass-scale examinations of population, for roentgenography in urology and other departments of clinics, where periodic observation of slow propagation of an X-ray contrast agent in the body is needed, and, optionally, for X-ray defectoscopy of arbitrary devices or for frontier and customs inspection of the luggage of passengers and cargoes.

PRIOR ART

WO 98/11722 (PCT/UA96/00016, priority date of 10 Sep. 1996) discloses an X-ray diagnostic system equipped with an X-ray converter based on at least two TV cameras rigidly fastened to a common base in such a way that their separate fields of view partly overlap each other and the joint field view of theirs overlaps the area of said converter. In this system:

optical inputs of all TV cameras are oriented towards the converter of X-radiation into visible light (this converter is made from such suitable material as cesium iodide or salts of rare-earth elements and the like and hereinafter designated as the "X ray-to-optical converter"), and electrical outputs of all TV cameras are connected through an ADC-unit to a multichannel corrector of geometric distortions, which provides synthesis of integral output video signal from fragmentary video signals.

The resolution of this integral output video signal is the higher, the more TV cameras are used in said converter. Moreover, this signal, after adjustment of said corrector, contains practically no distortions caused by unavoidable differences in the geometric shape and dimensions of individual TV cameras and their parts, and by inevitable errors in their mounting.

X-ray diagnostic systems equipped with said X-ray converters are convenient in manufacturing and servicing and are of a reasonable price, and the experience in their many years' practical application confirmed that:

first, an integral output video signal can be obtained with a frequency of not less than 25 frames per second, which is sufficient for angiographic examinations, second, the radiation dose absorbed by patient during one X-ray examination is reduced as a rule by a factor of 20 and more in comparison with the ordinary photofluorography, third, the protection of the medical or other operating staff is facilitated, because any display for the demonstration of images based on integral output video signals can be located at a safe distance from X-ray source, fourth, said images are convenient for recording and storing on high-capacity modern data carriers for the keeping of case histories and repeated reviews, and fifth, digital video records can be easily converted into usual images on the X-ray film by exposing it in front of a display suitable in the screen size. In fact, "Apparatus for printing multiform images . . . " has been designed for this purpose (see RU 22249 U1 and UA 1282 U). It is available at the CIS market now.

However, the same practical experience demonstrated that the quality of images based on integral output video signals is substantially dependent on:

first, optical disturbances which arise, in particular:

over illumination from external light sources, under action of parasitic light fluxes between TV cameras and the X-ray-to-optical converter and between adjacent TV cameras, and over distortion of light fluxes in optical channels of TV cameras, and second, the action on TV cameras of such X-radiation that isn't converted into the visible light, whose power can reach 70% (and at best is not less than 30%) of the initial power of this radiation.

Some of said disadvantages have been relatively easily eliminated or at least appreciably attenuated. Thus, the converter according to U.S. Pat. No. 6,002,743 was equipped with:

a housing made of X-ray-transparent material opaque for the visible light (in order to eliminate the illumination from external light sources), and a one-piece plate of X-ray-opaque lead glass installed between the X-ray-to-optical converter and optical inputs of TV cameras (in order to absorb the residual X-radiation).

Such plate protects TV cameras from said residual X-radiation the more efficiently, the greater its thickness. Accordingly, the reliability of the converter as a whole is markedly enhanced. However, this obvious improvement call out undesirable side effects, namely:

intensification of parasitic light fluxes between TV cameras and the X-ray-to-optical converter and between adjacent TV cameras and, as a result, additional distortions of light fluxes in optical channels of TV cameras.

Indeed, the brightness of that part of the total X-radiation flux which passed through the patient or another obstacle is inhomogeneous by itself and, what is particularly important, substantially differs from the brightness of the remaining part of said flux. Accordingly, the visible image on the X-ray-to-optical converter as well has parts differing in the brightness. The brightest parts give rise to an intense Lambert's radiation of light in broad solid angles. Corresponding light fluxes freely propagate in random directions in the lead glass plate and therefore only partly get to optical inputs of TV cameras, which are located exactly opposite said bright sections. Other parts of the light fluxes give rise to the parasitic illumination of adjacent TV cameras and, reflecting many times from converter parts (in particular from objective lenses of TV cameras) and propagating within the lead glass plate or passing through it, can get:

to optical inputs of random TV cameras of the converter, creating a random set of optical interferences in every diagnostic session, and to relatively dark zones of the X-ray-to-optical converter, creating a random illumination commensurable with the brightness of said zones.

These undesirable effects are especially pronounced when the angle of incidence of light rays from the X-ray-to-optical converter on surfaces of objective lenses of corresponding TV cameras exceeds the angle of total internal reflection in the lead glass. Moreover, in such cases the secondary reflection results in polarization of light.

U.S. Pat. No. 6,370,225 discloses a more perfect X-ray converter, which is most similar to the proposed below converter in subject matter. This known converter comprises of:

a light-proof housing, one of whose walls is X-ray-transparent, and the following units fastened one after another behind the wall:

an X-ray-to-optical converter, a polarizing filter, a filter of residual X-radiation in the form of a lead-glass plate, an unit of photodetector's objective lenses, where the number and placement of the objective lenses correspond to the number and placement of optoelectronic converters (in particular, TV cameras) in the photodetector, and said photodetector containing at least two optoelectronic converters having partly overlapping fields of view and separated electrical outputs for connecting to a system for processing of fragmentary video signals and their "sewing together" into an integral output video signal.

Along with above-indicated attributes, the following specific features characterize the known converter:

said lead-glass plate is on the side facing said objective lenses divided by blind slots intersecting at right angles into sections whose number is equal to the optoelectronic converters' number of the photodetector, the depth of said slots is of about 0.25 to 0.35 of the thickness of the lead-glass plate and the slots are filled with an opaque material, and each said objective lens has one input lens which abuts upon the lead-glass plate surface, three intermediate lenses separated by air gaps, and one output lens which abuts upon the photodetector surface.

One skilled in the art will appreciate that known X-ray converter solves the problem of improving the image quality by parts only and not efficiently enough, and the problem of enhancing the reliability is practically not solved. In fact:

the polarizing filter attenuates the polarized component of light reflected from the lead glass, but does not affect the remaining light flux, multi-lens optical systems of said objective lenses, where lenses are separated by air gaps, give rise to irregular reflections of practically unpolarized light onto said X-ray-to-optical converter, and darkened slots only reduce (but not exclude) a parasitic illumination of adjacent optoelectronic converters because of free motion of light beams in the not slotted part of the lead-glass plate.

Due to this, integral video signals can contain artifacts in the diagnostic picture. Moreover, said slots reduce down to unacceptable level not only the mechanical strength of the brittle lead-glass plate, but also the reliability of the converter as a whole.

SUMMARY OF THE INVENTION

The invention is based on the problem of creation, by improving the form, positional relationship and relative dimensions of parts, such X-ray converter that would secure effective suppression of internal interferences within optical channels and operating reliability at once.

This problem is solved in that in an X-ray converter having:

a light-proof housing, one of whose walls is X-ray-transparent, and following units fastened one after another behind this wall:

an X-ray-to-optical converter, a filter of residual X-radiation, an unit of objective lenses, each of which contains at least two one by one installed lenses for focusing a part of the light flux on the corresponding optoelectronic converter, and a photodetector containing at least two optoelectronic converters having partly overlapping fields of view and separated electrical outputs for connecting to a system for processing of fragmentary video signals and their "sewing together" into an integral output video signal, according to the invention, the light-proof housing is equipped with an additional light-opaque and X-ray-opaque partition that has through-holes, whose number and placement correspond to the number and placement of objective lenses and optoelectronic converters, and is rigidly fastened within said housing practically parallel to the X-ray-to-optical converter, the filter of residual X-radiation is formed as washers that are made from an X-ray-opaque light-transparent material and rigidly fastened within said through-holes of the additional partition, said additional partition is equipped with blinds, whose number and placement correspond to the number and placement of objective lenses and optoelectronic converters; these blinds are installed on such side of this partition that is opposite to said X-ray-to-optical converter, and length A of each said blind and distance D from the front (in the pass of X-rays) surface of said X-ray-to-optical converter to the plane of front (in the pass of light) end faces of the objective lenses are related by the ratio $A/D=(0.50\ldots0.95)$.

An X-ray converter equipped with above-mentioned additional and perfected parts allows at once:

first, to reduce the parasitic illumination of adjacent optoelectronic converters considerably, because lead-glass washers serving as the filter of residual X-radiation are optically insulated from one another in said partition, while the light reflected from parts of optical channels to the surface of the X-ray-to-optical converter and back mostly returns via the blinds into initial channels, and second, to enhance the operating reliability of the converter, because the X-ray load on optoelectronic converters is limited to only that insignificant part of the X-radiation, not converted into light, which can pass through washers of said filter, and the danger of a mechanical break-down of the filter is excluded practically.

It is preferable to select the A/D ratio within (0.55-0.90). This warrants the overlap of fields of view of the optoelectronic converters.

Further distinction consists in that said additional partition comprises of a lead plate and a supporting plate made from suitable rigid material. This warrants practically full absorption of such residual X-radiation, which does not get into said blinds, and sufficient strength and stability of the housing and fastened therein parts of optical channels.

Next distinctions consist in that each objective lens is equipped with at least one diaphragm for restriction of the light flux, and preferably, with three diaphragms installed respectively ahead of the input lens, between lenses, and after the output lens. These diaphragms additionally protect optoelectronic converters from light interferences that can arise because of repeated light reflections within optical channels.

And, finally, additional distinctions consist in that interior of the side housing walls, blinds on the inside, and diaphragms on both sides have black mat coatings, and surfaces of said washers of the filter of residual X-radiation and the lenses of said objective lenses have antireflecting coatings. Such coatings— serve as additional means for the suppression of random light interferences caused by light reflections within optical channels, and practically prevent decrease of the image brightness at field of view edges of each optoelectronic converters, which can occur under the diaphragms' action.

BRIEF DESCRIPTION OF THE DRAWINGS

The invention is further explained by a detailed description of the proposed device with references to accompanying drawings in which.

BEST MODE CARRYING OUT THE INVENTION

Figure 1:
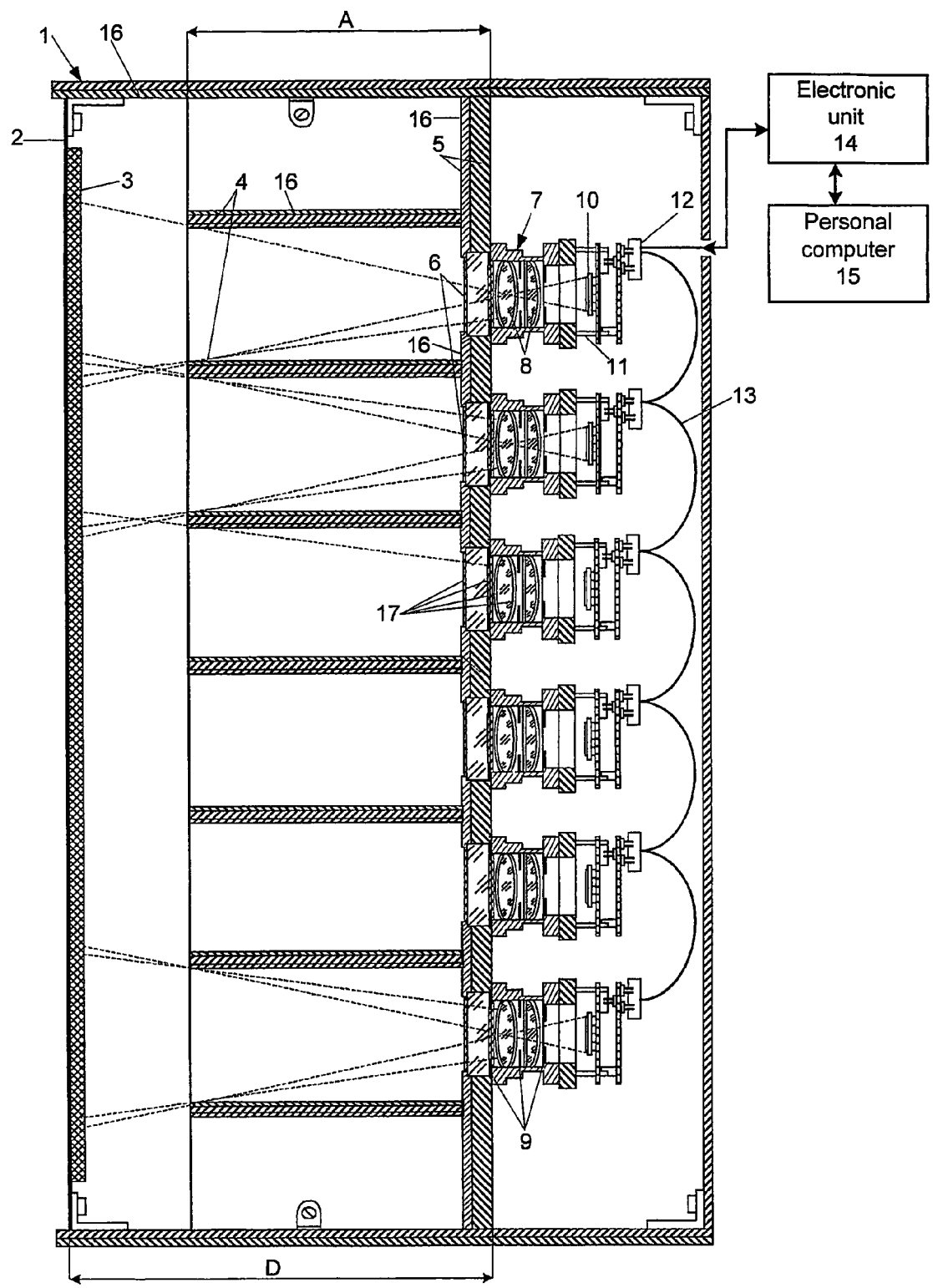
FIG. 1 is a sectional view of the X-ray converter in a plane containing geometrical axes of one of vertical rows of optoelectronic converters.

The X-ray converter in the simplest embodiment (see FIG. 1) contains at least:

a light-proof housing 1, one of whose end walls 2 is made from such X-ray transparent material as Getinaks or coal fiber-reinforced plastic etc., and following units fastened one after another behind said wall 2— an X-ray-to-optical converter 3 that is made from salts of rare-earth elements or cesium iodide usually and abuts upon the end wall 2 of the housing 1, blinds 4, whose number and placement correspond to the number and placement of indicated below objective lenses and optoelectronic converters; the blinds 4 are installed within the housing 1 so that "fields of view" of said optoelectronic converters partly overlap one another, an additional light-opaque and X-ray-opaque partition 5 that is rigidly fastened in housing 1 and serves as a support for said blinds 4 and other indicated below elements of optical channels; the partition 5 has through-holes closed by rigidly fastened (usually calked) washers 6 produced usually from such X-ray-opaque light-transparent material as lead glass (these washers 6 serve, in aggregate, as filter of residual X-radiation at the inputs into optical channels), objective lenses 7, whose number and placement correspond to the number and placement of indicated below optoelectronic converters; each such objective lens 7 has at least two separated by an air gap lenses 8 that are intended for the focusing of parts of the image on optoelectronic converters, and, as a rule, three (input, intermediate, and output) diaphragms 9 that are intended for limiting the light flux, optoelectronic converters 10, each of which is fastened on an own support in adjusting device 11 for installation on the optical axis of corresponding objective lens 7; these converters 10 are formed usually as commercially available TV cameras.

Electrical outputs of the optoelectronic converters 10 are formed as plug-and-socket connectors 12. They are through a flexible multiple-conductor cable 13 connected:

first, to an (not shown) electric power source, and second, to electronic unit 14 for correction of geometric distortions and "sewing together" of fragmentary video signals into output integral video signals for demonstration of images by a video monitor of suitable personal computer 15 and/or their recording on suitable digital image carrier.

Partition 5 has, as a rule, two (not especially designated) parts, namely:

an formed usually as a leaden plate absorber of such residual X-radiation that goes past the optical channels, and a supporting plate formed from such fast rigid material as duraluminum, steel, or any reinforced polymer etc.

As a rule, interior of side walls of the housing 1, all blinds 4 on the inside and all diaphragms 9 on both sides have black mat coating 16; and surfaces of the all said washers 6 and lenses 8 have antireflecting coatings 17.

It is clear for any person skilled in the art that blinds 4 must warrant partial overlap of fields of view of the adjacent optoelectronic converters 10 on X-ray-to-optical converter 3 (it is shown on FIG. 1 as intersection of light beams emitted from X-ray-to-optical converter 3 into objective lenses 7). Along with this condition, said blinds 4 are for:

minimization of decreasing of image brightness at edges of field of view of each optoelectronic converter 10 (even when objective lenses 7 have diaphragms 9), and substantial reducing of parasitic illumination of adjacent TV cameras by light repeatedly reflected from lenses 8 to X-ray-to-optical converter 3 and back.

Thereto, length A of blinds 4 is selected with account of distance D from the front (in the pass of X-rays) surface of X-ray-to-optical converter 3 to the plane of front (in the pass of light) end faces of objective lenses 7 in accordance with the ratio A/D=(0.50-0.95) and preferably (0.50-0.90).

Said ratios have been determined experimentally on a prototype X-ray converter, which had:

X ray-to-optical converter 3, based on gadolinium oxysulfide, a set of changeable blinds 4 of various heights A with black mat coatings 16 on their inside surfaces, light-opaque and X-ray-opaque partition 5 formed as fast joined 2.5 mm thick leaden plate and 8.0 mm thick duraluminum plate; this partition 5 had 36 through-holes 27 mm in diameter and such calked in said through-holes lead-glass washers 6 a 10.0 mm thick that are provided with antireflecting coatings 17 on both sides, objective lenses 7 each of which formed as set of glued-together lenses with antireflecting coatings 17 on their free surfaces, a photodetector formed as an lattice of 6×6=36 optoelectronic converters 10 (in particular, photodiode matrices produced by Japanese company "Sony") served for brightness measurements during experiments, electronic unit 14 for correction of geometric distortions and "sewing together" of fragmentary video signals into integral video signals; said unit 14 was produced by "Teleoptic" company (Kiev, Ukraine) and driven by software "Alpha-Teleoptic" of the same firm, and usual PC 15 equipped with a liquid-crystal video monitor.

In addition, the following devices has been used in experiments:

X-ray tube (model 2.5-50BD150) produced by Research-and-Production Association "Svetlana" (Sankt-Peterburg, Russia), produced by "MosRentgen" (Moscow, Russia) pulsed power source for feeding said tube; this source had anode voltage of 40-125 kV and operating current of 40-400 ma, collimator (i.e. leaden blinds) installed at the output of said X-ray tube to provide for uniform illumination of the whole receiving surface of the X-ray-to-optical converter 3, movable screen (not shown in drawings) formed as an X-ray-opaque leaden plate whose dimensions correspond to the maximum field of view of each optoelectronic converter 10 (in particular, 44×33 mm for each said photodiode matrix). This screen was intended for blocking of X-ray inputs into individual optical channels.

Dimension D was of 75 mm and remained unchanged in all experiments.

1. The measurement procedure has been carried out with account of two basic prerequisites established experimentally in the course of a long practical operation of several series of X-ray converters.

2. The first prerequisite consists in that the overlap of fields of view of adjacent optoelectronic converters 10 must be, as a rule—

3. no less than 3% in order to avoid an accidental loss of some part of diagnostic information, but 4. no more than 10% in order to avoid excessive losses of the resolution of the photodetector as a whole.

5. From the above it follows that length A of blinds 4 cannot be equal to dimension D (in order to exclude full insulation of optical channels).

6. Accordingly, the second prerequisite consists in that the blocking of X-ray input to each selected individual optical channel by said movable screen does not exclude the illumination of the photodiode matrix in such channel through adjacent optical channels. Due to this, the detection of light by the photodiode matrix under any optical channel that is screened from the X-radiation and the distribution of brightness within this matrix can serve as a criterion of efficiency of selection of A/D ratio.

The procedure of determination of acceptable limits of said ratio, based on these prerequisites, included:

(1) determination of the initial brightness of light in optically insulated channels at the use of a free X-ray-to-optical converter, (2) serial determination of brightness of light directly by each regularly scheduled photodiode matrix and its distribution with respect to the such matrix central zone (using software "Alpha-Teleoptic") in each optical channel, the X-ray input to which was temporarily closed by the movable leaden screen; this determination was executed:

(2.1.) first, at absence of the blinds 4, and, (2.2) further, using the blinds 4 of various length (and, accordingly, with various A/D ratios) down to complete overlap of the gap between X-ray-to-optical converter 3 and partition 5 and full insulation of optical channels.

Results of measurements are presented in the table below.

DEPENDENCY OF ILLUMINATION OF OPTICAL CHANNELS, CLOSED WITH RE MOVABLE LEADEN SCREEN, THROUGH ADJACENT OPTICAL CHANNELS ACCORDING TO A/D RATIO

| nos | A/D | Brightness, % of initial value | | | Remarks |
| --- | --- | --- | --- | --- | --- |
| | | at center | at left-hand boundary | at right-hand boundary | |
| 1 | 0 | 6.4 | 8.8 | 10.0 | Blinds absent |
| 2 | 0.22 | 4.0 | 5.6 | 6.2 | Blinds not effective |
| 3 | 0.42 | 2.0 | 3.0 | 3.2 | |
| 4 | 0.50 | 1.6 | 2.2 | 2.5 | Blinds reduce parasitic illumination to acceptable level |
| 5 | 0.55 | 1.2 | 1.8 | 2.0 | Blinds effectively reduce parasitic illumination of adjacent optical channels and flatten |
| 4 | 0.62 | 0.8 | 1.6 | 1.8 | |
| 6 | 0.75 | 0.4 | 0.8 | 1.0 | |
| 7 | 0.83 | 0.3 | 0.6 | 0.7 | brightness on working surface of optoelectronic converters |
| 8 | 0.90 | 0.2 | 0.4 | 0.5 | Blinds slightly restrict field of view of photodiode matrices |
| 9 | 0.95 | 0.1 | 0.2 | 0.3 | Sewing of fragments together into integral image is feasible |
| 10 | 1.0 | 0 | 0 | 0 | Blinds insulate optical channels and divide image into separate fragments |

As is shown in the table, appreciable decrease of the parasitic illumination of adjacent optical channels and flattening of the brightness on the working surface of optoelectronic converters take place at the ratio A/D=0.50 and reach a practically possible maximum at A/D=0.95, when the overlap of fields of view of adjacent optoelectronic converters 10 approaches 2%. Already in this range, A/D=(0.50-0.95), the software for identification and elimination of such random optical interferences which can affect the quality of the sewing together fragmentary video signals into integral video signals (and images of objects being diagnosed or checked, corresponding to them) becomes needless.

In practice, however, it is preferable to set the A/D ratio at between 0.55 and 0.90 when random optical interferences are negligible and cannot affect the quality of the medical diagnosis and all the more of the quality of the X-ray flaw detection or of the border and customs inspection of the luggage of passengers and cargoes.

Figure 2:
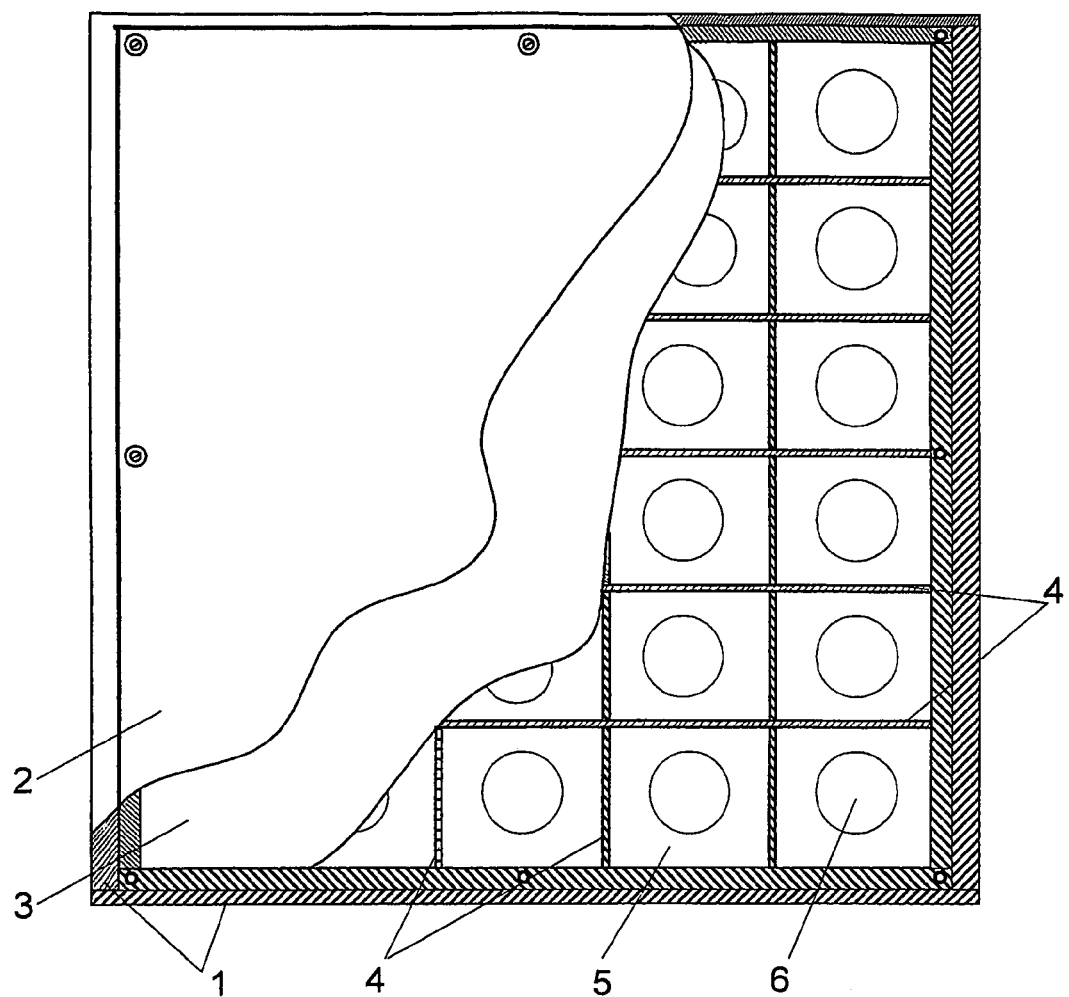
FIG. 2 is a schematic diagram of optoelectronic converters' placement with respect to the X-ray-to-optical converter (when fore-wall of the X-ray converter housing and X-ray-to-optical converter are partly "broken away").

The above-described X-ray converter operates as follows:

At the assembling or before the start of operation, optoelectronic converters 10 are with the aid of adjusting devices 11 (see FIG. 1) installed in output planes of objective lenses 7 in such a manner that centers of light-sensitive surfaces of converters 10 correspond to foci of objective lenses 7, each of which is placed opposite to certain part of the surface of X-ray-to-optical converter 3 (see FIG. 2). To facilitate the adjustment, known calibrating test objects (spatial phantoms) can be used, as indicated, e.g., in WO 98/11722.

The adjusted converter is installed into the device for the X-ray diagnostics (or flaw detection, or inspection) so that the object of investigation can be in the gap between the output of the X-ray tube and the X-ray-transparent wall 2 of lightproof housing 1. Then, at each tube activation the X-ray flux will act on X-ray-to-optical converter 3, which serves as a Lambert's light source and generates a light flux differentiated in the brightness because of interaction with the object of diagnostics (or flaw detection, or inspection).

Blinds 4 divide this light flux into separate beams, which through washers 8 made of lead glass that filters off the residual X-radiation and objective lenses 7 get onto light-sensitive surfaces of optoelectronic converters 10. They generate analog electric signals which correspond to partly overlapping fragments of the image formed on X-ray-to-optical converter 3. Said signals, via plug-and-socket connectors 12 and flexible multiple-conductor cable 13, arrive to electronic unit 14, which converts them into a digital form, corrects geometric distortions, and "sews together" fragmentary digital video signals into integral digital video signals for a subsequent demonstration of images on the video monitor of PC 15 and/or recording on suitable digital storage devices.

Specific features of operation of the described X-ray converter are as follows.

Light- and X-ray-opaque partition 5 practically fully absorbs that part of the residual X-radiation, which does not get onto lead-glass washers 6 and fully excludes leakages of light between said washers 6.

Blinds 4 drastically reduce the parasitic illumination of adjacent optical channels with light reflected from objective lenses 7 and/or optoelectronic converters 10 to X-ray-to-optical converter 3 and back.

Diaphragms 9 additionally suppress random optical interferences (particularly in the form of light reflected from surfaces of optoelectronic converters 10). Black mat coatings 16 of side walls of housing 1, of blinds 4 on the inside, and of diaphragms 9 on both sides serve for the same purpose (but for any light interferences).

And, finally, anti-reflection coatings 17 reduce the reflectivity of surfaces of washers 6 and lenses 8 practically by an order of magnitude.

INDUSTRIAL APPLICABILITY

The industrial applicability of the X-ray converter is due to:
first, possibility of its production with the use of modern components in various configurations, and
second, possibility of its use for the synthesis of integral (with no visible joints) images of objects being diagnosed with a high resolution.

The invention claimed is:
1. An X-ray converter comprising:
a light-proof housing, one of whose walls is X-ray transparent, and the following units fastened one after another behind this wall:
an X-ray-to-optical converter of the X-radiation into visible light,
a filter of residual X-radiation,
an unit of objective lenses, each of which contains at least two one by one installed lenses for focusing a part of the light flux on the corresponding optoelectronic converter, and
a photodetector containing at least two optoelectronic converters having partly overlapping fields of view and separated electrical outputs for connection to a system for fragmentary video signals processing and their "sewing together" into an integral output video signal, characterized in that
the light-proof housing is equipped with an additional light-opaque and X-ray-opaque partition that has through-holes, whose number and placement correspond to the number and placement of objective lenses and optoelectronic converters, and is rigidly fastened within said housing practically parallel to the X-ray-to-optical converter,
the filter of residual X-radiation formed as washers that are made from an X-ray opaque light-transparent material and rigidly fastened within said through-holes of the additional partition,
said additional partition is equipped with blinds, whose number and placement correspond to the number and placement of objective lenses and optoelectronic converters; these blinds are installed on such side of this partition that is opposite to said X-ray-to-optical converter, and
length A of each blind and distance D from the front (following the pass of X-rays) surface of said X-ray-to-optical converter to the plane of front (following the pass of light) end faces of objective lenses are related by the ratio $A/D = (0.50-0.95)$.

2. The X-ray converter of claim 1 characterized in that said ratio is of $A/D = (0.55-0.90)$.

3. The X-ray converter of claim 2 characterized in that said additional partition comprises of a lead plate and a supporting plate made from suitable rigid material.

4. The X-ray converter of claim 3 characterized in that each objective lens is equipped with at least one diaphragm for restriction of the light flux.

5. The X-ray converter of claim 4 characterized in that each objective lens has three diaphragms installed ahead of the input lens, between lenses, and after the output lens.

6. The X-ray converter of claim 2 characterized in that surfaces of said washers of the filter of residual X-radiation and the lenses of said objective lenses have anti-reflecting coatings.

7. The X-ray converter of claim 1 characterized in that said additional partition comprises of a lead plate and a supporting plate made from suitable rigid material.

8. The X-ray converter of claim 7 characterized in that each objective lens is equipped with at least one diaphragm for restriction of the light flux.

9. The X-ray converter of claim 8 characterized in that each objective lens has three diaphragms installed ahead of the input lens, between lenses, and after the output lens.

10. The X-ray converter of claim 9 characterized in that interior of the side housing walls, blinds on the inside, and diaphragms on both sides have black matte coatings.

11. The X-ray converter of claim 9 characterized in that surfaces of said washers of the filter of residual X-radiation and the lenses of said objective lenses have anti-reflecting coatings.

12. The X-ray converter of claim 8 characterized in that interior of the side housing walls, blinds on the inside, and diaphragms on both sides have black matte coatings.

13. The X-ray converter of claim 12 characterized in that surfaces of said washers of the filter of residual X-radiation and the lenses of said objective lenses have anti-reflecting coatings.

14. The X-ray converter of claim 8 characterized in that surfaces of said washers of the filter of residual X-radiation and the lenses of said objective lenses have anti-reflecting coatings.

15. The X-ray converter of claim 7 characterized in that surfaces of said washers of the filter of residual X-radiation and the lenses of said objective lenses have anti-reflecting coatings.

16. The X-ray converter of claim 1 characterized in that surfaces of said washers of the filter of residual X-radiation and the lenses of said objective lenses have anti-reflecting coatings.

* * * * *